(12) United States Patent
Lyden

(10) Patent No.: US 7,580,749 B2
(45) Date of Patent: ***Aug. 25, 2009

(54) METHOD FOR MONITORING END OF LIFE FOR BATTERY

(75) Inventor: Michael J. Lyden, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/779,779

(22) Filed: Jul. 18, 2007

(65) Prior Publication Data

US 2007/0265672 A1 Nov. 15, 2007

Related U.S. Application Data

(60) Division of application No. 10/631,995, filed on Jul. 31, 2003, now Pat. No. 7,251,527, which is a division of application No. 10/093,141, filed on Mar. 6, 2002, now Pat. No. 6,654,640, which is a continuation of application No. 09/670,653, filed on Sep. 27, 2000, now abandoned, which is a division of application No. 08/929,629, filed on Sep. 15, 1997, now Pat. No. 6,167,309.

(51) Int. Cl.
*A61N 1/37* (2006.01)
(52) U.S. Cl. .................. 607/29; 607/27; 607/9
(58) Field of Classification Search ............ 607/9, 607/27, 29
See application file for complete search history.

(56) References Cited

U.S. PATENT DOCUMENTS

| 3,103,617 | A | 9/1963 | Schneider et al. |
| 3,300,658 | A | 1/1967 | Slusher |
| 4,031,899 | A | 6/1977 | Renirie |
| 4,134,408 | A | 1/1979 | Brownlee et al. |
| 4,259,639 | A | 3/1981 | Renirie |
| 4,276,883 | A | 7/1981 | McDonald et al. |
| 4,290,429 | A | 9/1981 | Blaser |

(Continued)

FOREIGN PATENT DOCUMENTS

EP 0739645 10/1996

OTHER PUBLICATIONS

Parsonnet, V. , "Cardiac pacing and pacemakers VII. Power sources for implantable pacemakers. Part I.", *American Heart Journal*, 94 (4), (Oct. 1977), pp. 517-528.

(Continued)

*Primary Examiner*—Angela D Sykes
*Assistant Examiner*—Joseph Stoklosa
(74) *Attorney, Agent, or Firm*—Schwegman, Lundberg & Woessner, P.A.

(57) ABSTRACT

A system is described. The system includes a lithium battery, a charge storage capacitor electrically connected to the lithium battery, a first device, and at least one second device. The first device is electrically connected to the lithium battery and is powered by the lithium battery. The at least one second device is attached to the charge storage capacitor and adapted to read a rate of charge storage in the charge storage capacitor or to calculate the rate of charge storage by measuring both a time of charging and a charge stored or added to the charge storage capacitor during the time of charging.

25 Claims, 4 Drawing Sheets

U.S. PATENT DOCUMENTS

| | | | |
|---|---|---|---|
| 4,323,075 | A | 4/1982 | Langer |
| 4,345,604 | A | 8/1982 | Renirie |
| 4,408,607 | A | 10/1983 | Maurer |
| 4,548,209 | A | 10/1985 | Wielders et al. |
| 4,556,061 | A | 12/1985 | Barreras et al. |
| 4,606,350 | A | 8/1986 | Frost |
| 4,659,994 | A | 4/1987 | Poljak |
| 4,672,973 | A | 6/1987 | Hofke |
| 4,709,202 | A | 11/1987 | Koenck et al. |
| 4,830,006 | A | 5/1989 | Haluska et al. |
| 4,868,908 | A | 9/1989 | Pless et al. |
| 4,873,490 | A | 10/1989 | Hecht et al. |
| 4,952,864 | A | 8/1990 | Pless et al. |
| 4,958,641 | A | 9/1990 | Digby et al. |
| 5,030,849 | A | 7/1991 | Brokaw |
| 5,083,562 | A | 1/1992 | De Coriolis et al. |
| 5,137,021 | A | 8/1992 | Wayne et al. |
| 5,159,520 | A | 10/1992 | Toyooka et al. |
| 5,184,616 | A | 2/1993 | Weiss |
| 5,265,588 | A | 11/1993 | Nelson |
| 5,285,779 | A | 2/1994 | Cameron et al. |
| 5,323,068 | A | 6/1994 | Freitas |
| 5,369,364 | A | 11/1994 | Renirie et al. |
| 5,370,668 | A | 12/1994 | Shelton et al. |
| 5,391,193 | A | 2/1995 | Thompson |
| 5,402,070 | A | 3/1995 | Shelton et al. |
| 5,424,683 | A | 6/1995 | Takahashi |
| 5,447,522 | A | 9/1995 | Chang et al. |
| 5,458,624 | A * | 10/1995 | Renirie et al. ............ 607/29 |
| 5,483,165 | A | 1/1996 | Cameron et al. |
| 5,488,553 | A | 1/1996 | Renger |
| 5,496,353 | A | 3/1996 | Grandjean et al. |
| 5,527,630 | A | 6/1996 | Nagata et al. |
| 5,528,087 | A | 6/1996 | Sibata et al. |
| 5,562,595 | A | 10/1996 | Neisz |
| 5,591,213 | A | 1/1997 | Morgan |
| 5,596,987 | A | 1/1997 | Chance |
| 5,675,258 | A | 10/1997 | Kadouchi et al. |
| 5,690,685 | A | 11/1997 | Kroll et al. |
| 5,700,280 | A | 12/1997 | Silvian |
| 5,713,936 | A | 2/1998 | Staub |
| 5,721,482 | A | 2/1998 | Benvegar et al. |
| 5,741,307 | A * | 4/1998 | Kroll ............ 607/5 |
| 5,769,873 | A | 6/1998 | Zadech |
| 5,772,689 | A | 6/1998 | Kroll |
| 5,779,631 | A | 7/1998 | Chance |
| 5,800,472 | A | 9/1998 | Mann |
| 5,812,383 | A | 9/1998 | Majid et al. |
| 5,869,970 | A | 2/1999 | Palm et al. |
| 5,904,705 | A | 5/1999 | Kroll et al. |
| 5,959,371 | A | 9/1999 | Dooley et al. |
| 6,018,227 | A | 1/2000 | Kumar et al. |
| 6,045,941 | A | 4/2000 | Milewits |
| 6,108,579 | A | 8/2000 | Snell et al. |
| 6,167,309 | A | 12/2000 | Lyden |
| 6,584,355 | B2 | 6/2003 | Stessman |
| 6,631,293 | B2 | 10/2003 | Lyden |
| 6,654,640 | B2 * | 11/2003 | Lyden ............ 607/29 |
| 7,251,527 | B2 | 7/2007 | Lyden |
| 2004/0024426 | A1 | 2/2004 | Lyden |

OTHER PUBLICATIONS

Ryan, J. G., "A Four Chip Implantable Defibrillator/Pacemaker Chipset", *Proceedings of the IEEE 1989 Custom Integrated Circuits Conference*, San Diego, CA,(1989),7.6.1-7.6.4.

Sherman, Don , "Measure resistance and capacitance without an A/D", *Philips Semiconductors Application Note AN449*, Philips Semiconductors, Sunnyvale, CA,(Dec. 1993),pp. 2540-2553.

Takeuchi, E. S., et al., "Energy Storage and Delivery", *Implantable Cardioverter Defibrillators: A Comprehensive Textbook*, edited by N.A. Mark Estes III et al., (1994),123-132.

Takeuchi, E. S., et al., "Lithium/Silver Vanadium Oxide Batteries for Implantable Defibrillators", *Pace*, 11, (Nov. 1988),2035-2039.

"U.S. Appl. No. 09/670,653 final office action mailed Nov. 7, 2001", 6 pgs.

"U.S. Appl. No. 09/670,653 Response filed Mar. 6, 2002 final office action mailed Nov. 7, 2001", 3 pgs.

"U.S. Appl. No. 09/840,408 non-final office action mailed Sep. 12, 2002", 9 pgs.

"U.S. Appl. No. 09/840,408 Notice of allowance mailed May 5, 2003", 4 pgs.

"U.S. Appl. No. 09/840,408 Response filed Jan. 13, 2003 non-final office action mailed Sep. 12, 2002", 15 pgs.

"U.S. Appl. No. 09/665,235 Notice of Allowance mailed Feb. 22, 2002", 4 pgs.

"U.S. Appl. No. 10/680,008 final office action mailed Jul. 16, 2007", 8 pgs.

"U.S. Appl. No. 10/680,008 non-final office action mailed Nov. 16, 2006", 7 pgs.

"U.S. Appl. No. 10/680,008 Response filed Feb. 16, 2007 non-final office action mailed Nov. 16, 2006", 10 pgs.

"U.S. Appl. No. 10/093,141 Amendment Under 37 CFR 1.312 mailed Jul. 21, 2003", 6 pgs.

"U.S. Appl. No. 10/093,141 Non Final Office Action mailed Dec. 4, 2002", 9 pgs.

"U.S. Appl. No. 10/093,141 Response filed Mar. 4, 2003 to Non Final Office Action mailed Dec. 4, 2002", 12 pgs.

"U.S. Appl. No. 10/093,141 Notice of Allowance mailed Apr. 21, 2003", 5 pgs.

"U.S. Appl. No. 10/631,995 Non Final Office Action mailed Nov. 16, 2006", 12 pgs.

"U.S. Appl. No. 10/631,995 Notice of Allowance mailed Mar. 23, 2007", 4 pgs.

"U.S. Appl. No. 10/631,995 Response filed Feb. 16, 2007 to Non Final Office Action mailed Nov. 16, 2006", 11 pgs.

"U.S. Appl. No. 10/680,008 Response filed Oct. 25, 2007 to Final Office Action Mailed Jul. 16, 2007", 13 Pages.

"U.S. Appl. No. 10/680,008 Final Office Action mailed Nov. 28, 2007", 10 pgs.

"Final Office Action Mailed Jul. 16, 2007 in U.S. Appl. No. 10/680,008", 8 pgs.

"U.S. Appl. No. 10/680,008 Notice of Allowance mailed Nov. 28, 2008", 8 pgs.

* cited by examiner

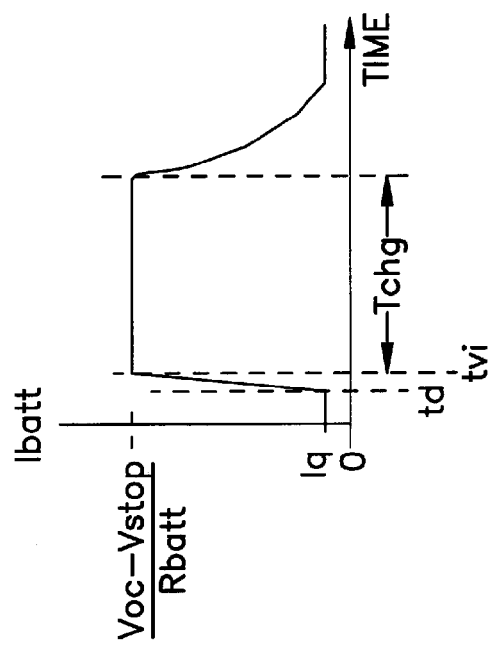
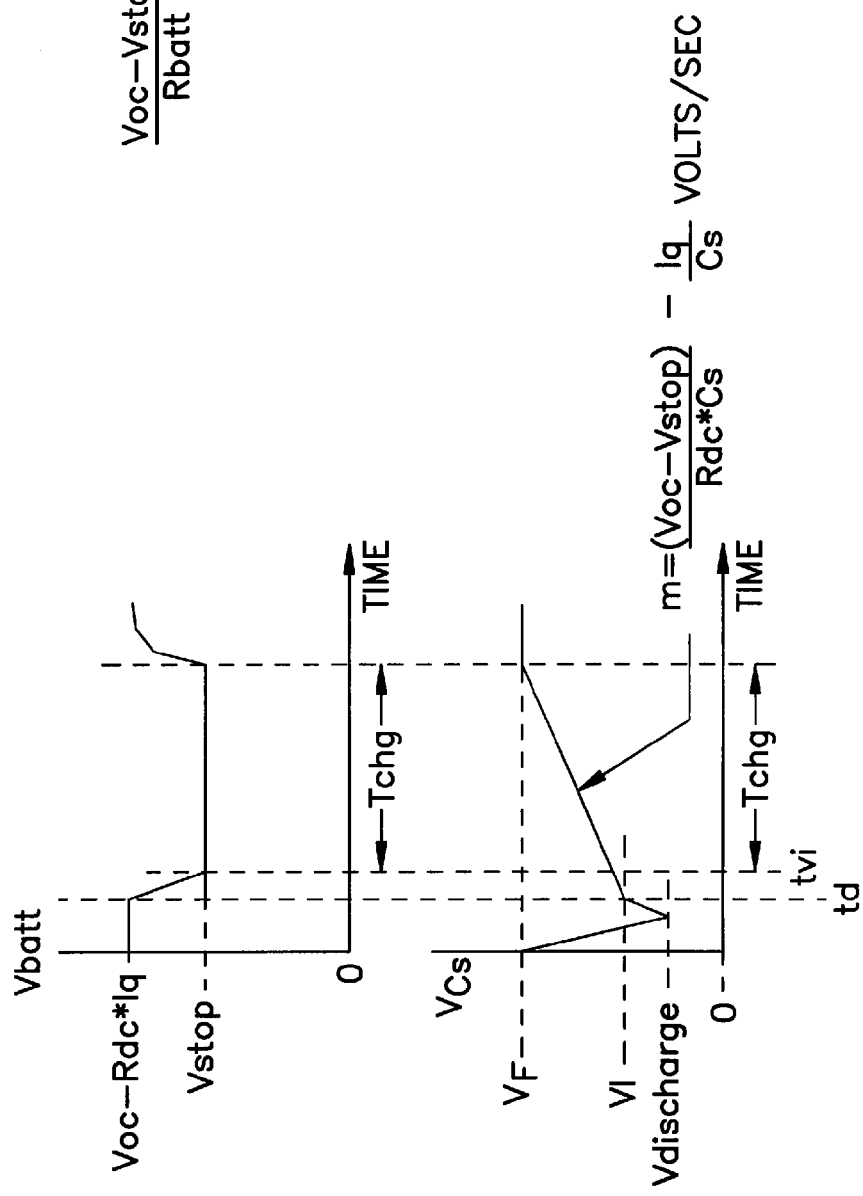
FIG. 3C
FIG. 3B

METHOD FOR MONITORING END OF LIFE FOR BATTERY

CROSS-REFERENCE TO RELATED APPLICATION(S)

This application is a divisional of U.S. patent application Ser. No. 10/631,995, filed on Jul. 31, 2003, now issued as U.S. Pat. No. 7,251,527, which is a division of U.S. patent application Ser. No. 10/093,141, filed on Mar. 6, 2002, now issued as U.S. Pat. No. 6,654,640, which is a continuation of U.S. patent application Ser. No. 09/670,653, filed on Sep. 27, 2000, now abandoned, which is a division of U.S. patent application Ser. No. 08/929,629, filed on Sep. 15, 1997, now issued as U.S. Pat. No. 6,167,309, the specifications of which are incorporated herein by reference.

FIELD OF THE INVENTION

The present invention relates to a method of determining when the end of life of a battery is approaching, and circuitry which may be used with that process. The invention particularly relates to such methods where access to the battery for conventional testing means is not readily available, where maintenance of sufficient levels of power from the battery are important with minimal interruption, and for monitoring of battery power in pacemakers.

BACKGROUND OF THE ART

Over the last several decades, the lithium-iodine battery has been widely adopted as a power source for the pacemaker industry, as well as other applications. Indeed, the broad use of this battery system in the pacemaker industry has resulted in it becoming substantially the standard power source for that industry. Well over 1,000,000 such batteries have already been implanted. The lifetime of such cells is not great enough to outlast the patient, so the industry has experienced occurrences where such batteries have come to their End Of Life (EOL) under nominal loads and normal circumstances. In addition to the actual replacement experiences of depleted batteries, methods have been developed for approximating the EOL curve of such batteries. It has become evident that there is a great need for matching or interfacing the device being powered by the battery with the parameters of battery behavior to optimize EOL operation.

In the practice of the invention of this application, reference is made to "lithium systems," meaning lithium-type battery cells. As pointed out in the article of Parsonnet et al., American Heart Journal, October 1977, Vol. 94, No. 4, pp. 517-528, in 1977 there were at least 5 types of lithium systems in widespread use, including lithium iodine types such as made by Wilson Greatbatch, Ltd. and Catalyst Research Corporation. Today an even wider number and variety of lithium batteries are available. This invention is directed particularly, but without limitation, to battery systems, especially the lithium battery systems characterized by having an internal impedance characteristic curve which is initially substantially linear as a function of energy depletion, but which asymptotically approaches an energy production (output) limit and increasing internal (e.g., DC) resistance. This total output maximum and high internal impedance is found near, but well before EOL. At that time, the linear characteristic relationship between energy depletion and internal impedance exhibits a knee and internal impedance rises rapidly. This characteristic of lithium-type sources is discussed in my U.S. Pat. No. 4,031,899 which patent is incorporated herein by reference. In the lithium iodine type battery, the cell cathode may consist of molecular iodine weakly bonded to polyvinyl pyridine (P2VP). At beginning of battery life in this type of system, there are about 6 molecules of iodine to each molecule of P2VP. No electrolyte, as such, is included in construction of the cell, but a lithium iodine (LiI) electrolyte layer forms during cell discharge, between the anode and cathode. The LiI layer presents an effective internal impedance to $Li^+$ ions which travel through it. Since the LiI layer grows with the charge drawn from the battery, or milliamp hours (mAh), this component of the battery impedance increases linearly as a function of mAh (i.e., as a function of cell energy depletion). In the pacemaker environment, since there is constant (but not uniform) energy depletion, this component of the internal impedance increases continually with time. However, and particularly for a demand pacer which at any time may or may not be delivering stimulus pulses, the increase of this component is not linear with time, due to the fact that current drain is not uniformly constant.

For the lithium iodine type cell, there is another component of internal impedance which is caused by depletion of iodine in the cathode. The cathode is essentially a charge transfer complex of iodine and P2VP, and during discharge of the cell iodine is extracted from this complex. In the beginning there are about 6 molecules of iodine to each molecule of P2VP. During extraction of iodine from the complex, the resistance to this procedure is low until the point is reached where about only 2 molecules of iodine are left for each molecule of P2VP, at which point this impedance rises very sharply. This gives rise to a non-linear internal impedance component which, for the lithium system, is called variously the depletion resistance, the depolarizer resistance, the charge transfer complex resistance, or the pyridine resistance. By whatever name, the combination of the non-linear component with the linear component produces the impedance characteristic with a knee occurring toward EOL, the knee being caused by the reaching of depletion of available charge carriers from the cathode.

The pacer industry is aware of the potential problem of determining EOL. Since the internal impedance of the source rises drastically after the knee, the battery may have very little or no useful lifetime left after the knee has been reached and passed. Some pacer manufacturers have predicated their design for determining EOL upon detection of the battery output voltage, which voltage comprises the constant open circuit voltage minus the drop caused by the current drain across the internal resistance. However, this is a highly tenuous and very unsatisfactory premise for determining EOL, due to the fact that actual current drain near EOL cannot be predicted nor directly measured with ease. For any manufacturer's pacer which is implanted and used in combination with a given electrode, there will be a variation in the effective load as seen by the lithium battery, and a resulting variation in the overall current drain. Accordingly, if the EOL design is predicated upon sensing voltage drop to a given level, there can be very little assurance that the level chosen will closely and accurately correspond to the knee of the cell curve.

One lithium cell manufacturer, Catalyst Research Corporation, in a paper presented to the Workshop on Reliability Technology For Cardiac Pacemakers, October, 1977, pointed out that for such batteries, sensing of the battery internal resistance is more reliable than voltage sensing. The position that cell resistance rather than cell voltage is a better warning indicator is based upon the observation that the resistance characteristic has a much less steep EOL curve. Stated differently, at low currents typical for pacers, plots of resistance against time give more warning than plots of voltage against time. If voltage characteristics for different current drains are plotted, the knees are observed to have a fairly wide variation, meaning that the voltage at which the knee might appear is subject to substantial variation as a function not only of the particular battery being used but also the load being drawn by the pacer. On the other hand, plots of resistance indicate that the knee varies over a smaller range of values of internal resistance. Since the current drain may vary by as much as a factor of 5 to 10 due to different electrode loads (which may be varied between similar units by pre-programming), the variation in voltage may be as much as five to ten times as great as the variation of internal resistance. Monitoring the internal resistance provides a direct indication of the state of the battery, whereas monitoring the output voltage gives only a secondary indication, reflecting both the state of the battery and the operating condition of the pacer. This condition, it is anticipated, will be even more emphasized with the development of new, thin, large area batteries and cells which generally have steeper EOL slopes.

U.S. Pat. No. 4,031,899 discloses a circuit which can be programmed to provide an indication of the internal resistance of the lithium battery cell. A switching circuit is used which alternately connects the relatively high current drain output circuitry and the relatively low current drain remainder of the circuit. By adjusting the duty cycle of the switching function, the voltage transferred from the battery to the respective circuits may be programmed to be substantially constant until the resistance reaches the predicted value correspondingly to the knee of the curve, after which there is a programmed drop. Since the oscillator rate is linear as a function of delivered voltage, a programmed drop in frequency can be used to indicate that the battery resistance has reached the level where the knee was expected. This feature provides a decided advantage over EOL designs which sensed voltage. The invention disclosed in U.S. Pat. No. 4,259,639 is described as having the added advantage that the exact resistance value at the knee need not be anticipated ahead of time. Even though the depletion resistance component is very predictable, the total value of the internal resistance at the time the knee is reached will be subject to some statistical variation so that EOL cannot be accurately predicted by simply monitoring total battery internal resistance. What is acutely needed in the pacer industry is a means for providing an accurate indication of the EOL and more preferably an accurate identification of an Elective Replacement Time (ERT) when a battery has reached a sufficiently depleted level that replacement procedures should be scheduled at a convenient time in a defined future period. The same need exists in other industries, such as electronic computers and space vehicles where batteries are used to maintain power during shut off of normal power or in emergencies.

U.S. Pat. No. 4,259,639 describes an improved method and circuitry means for detecting the occurrence of the knee of the curve of the resistance characteristic of a battery source having non-linear energy depletion characteristics. The circuit interfaces with a battery and is designed to measure that component of the internal resistance, which causes the knee in the internal resistance characteristics, and to provide an output which is useful for control of the device being driven by the battery. In the preferred embodiment, a high speed switching circuit is provided for measuring short circuit current drain from the battery over a small time duration, so that the short circuit current reflects the depletion component of the resistance which causes the knee, and does not reflect the internal resistance component. The circuit utilizes the fact that the electrical representation of the battery source comprises the linearly increasing resistance component in parallel with an effective capacitance, such that for very short samples of short circuit current from the battery, the linear component is shunted. By comparing the sampled short circuit with a predetermined value corresponding to a given level of the depletion resistance, which level is selected to clearly indicate the knee of the resistance characteristic, there is obtained an unambiguous indication that the battery is near end of life. One problem with this design is the need to essentially close down the electronics of the system, impress a significant voltage through the battery section to effectively override any transient current or signals, and read the data while the system is closed. In systems where continuous performance or minimally interrupted performance of power flow and system performance is required (as in pacemakers, difficult to replace battery systems, and the like), unnecessary shut down of the system in periodic or even infrequent intervals to test for battery depletion involves an element of risk that can not always be justified.

BRIEF DESCRIPTION OF THE DRAWINGS

FIGS. 3A, 3B and 3C show an example of Pacemaker Battery Charge-time measurement for the paging circuit shown.

SUMMARY OF THE INVENTION

Figure 1:
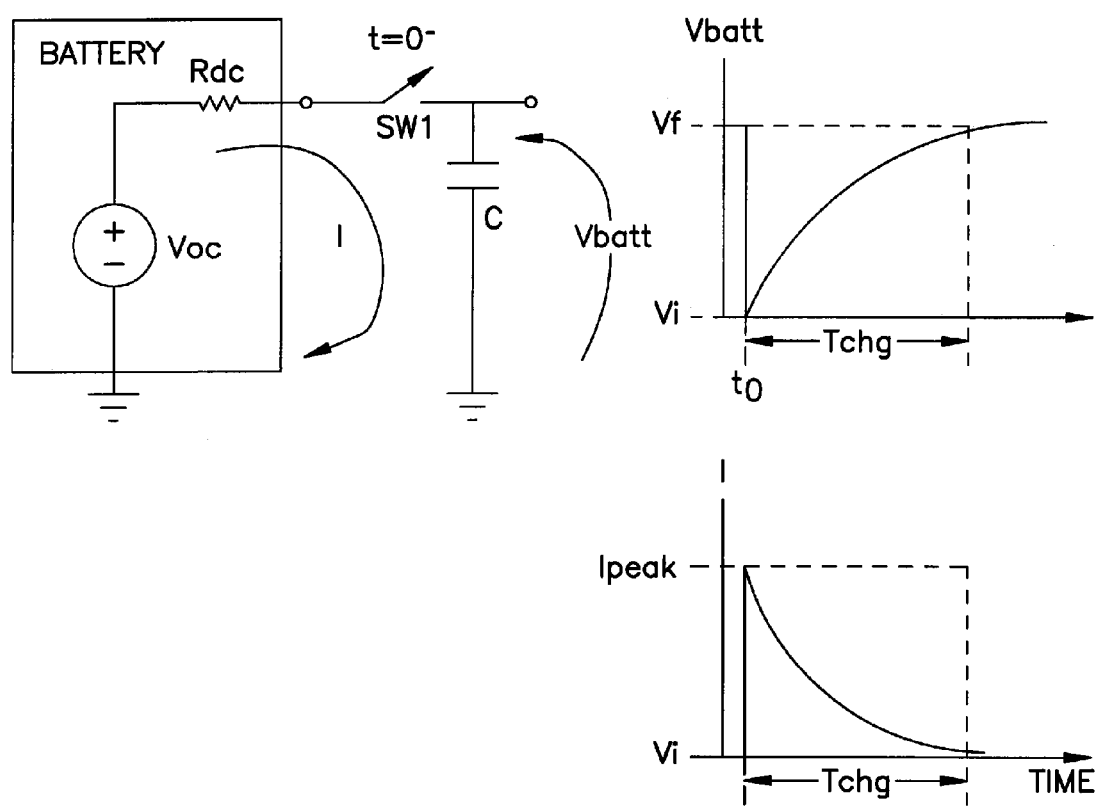
FIG. 1 shows two graphs of Simple Capacitive Charge Time Measurement to evaluate Battery Internal Impedance.

A system is described which has a battery, a device which is powered by said battery in an episodic manner, and a charge storage capacitor, said system having attached to said charge storage capacitor a device or devices capable of:
  a) reading the rate of charge storage or
  b) measuring both time and charge stored or added to said charge storage capacitor so that a rate of charge storage may be calculated.

The use of this system allows for easy estimation of the estimated replacement time for the battery, particularly for a lithium battery in a pacing device.

A process for estimating a level of energy depletion in the system may comprise
  a) finding a relatively quiescent period in powering of said device in said episodic manner
  b) determining a rate of charging in said storage capacitor during said quiescent period, and
  c) correlating said rate of charging in said storage capacitor to a value of internal impedance in said battery through a comparison with known relationships for said battery and rate of charging to determine a value for the internal impedance of said battery.

The present invention also describes an electrically powered system having a battery, especially a lithium battery, said battery characterized by having an internal impedance characteristic curve which is initially substantially linear as a function of energy depletion, but which asymptotically approaches an energy production (output) limit and increasing internal impedance. This total output maximum and high internal impedance is found near, but well before EOL. At that time, the linear characteristic relationship between energy depletion and internal impedance exhibits a knee and internal impedance rises rapidly. The preferred systems comprise a lithium battery, a device which is powered by said lithium battery in an episodic (e.g., non-constant, non-linear) manner, and a charge storage capacitor. The system has attached to said charge storage capacitor a device or devices capable of:
  a) reading the rate of charge storage or
  b) measuring both time and charge stored or added to said charge storage capacitor so that a rate of charge storage may be calculated.

A cardiac pacing system is described having a lithium battery, a device which delivers electric current to a patient, which device is powered by said lithium battery in an episodic manner, and a charge storage capacitor, said system having attached to said charge storage capacitor a device or devices capable of:
  a) reading the rate of charge storage or
  b) measuring both time and charge stored or added to said charge storage capacitor so that a rate of charge storage may be calculated.

A cardiac pacing system is described having a lithium battery, a device which delivers electric current to a patient, which device is powered by said lithium battery in an episodic manner, and a charge storage capacitor, said system having attached to said charge storage capacitor a device or devices capable of:
  a) reading the rate of charge storage or
  b) measuring both time and charge stored or added to said charge storage capacitor so that a rate of charge storage may be calculated.

In describing an episodic charge delivery, it is meant that at least one element of the device powered by the battery is powered in an episodic, as opposed to a continuous, manner. A system which has, for example, two elements, one powered in a continuous manner and the other powered in an episodic manner, is a system with an episodic charge delivery since at least one drain on the battery is episodic.

Also described is a process for using these types of systems. The process estimates a level of power depletion in a system having a lithium-type battery, a cardiac pacing device which is powered by said lithium battery in an episodic manner, and a charge storage capacitor, said system having attached to said storage capacitor a device or devices capable of:
  a) reading (including outputting to a reading device) the rate of charge storage or
  b) measuring both time and charge stored or added to said charge storage capacitor (or outputting such values to a reader) so that a rate of charge storage may be calculated.

The process then comprises:
  i) finding a relatively quiescent period in powering of said device in said episodic manner,
  ii) determining a rate of charging in said storage capacitor during said quiescent period, and
  iii) correlating said rate of charging in said storage capacitor to a value of Internal Impedance (e.g., DC or AC) in said battery through a comparison with known relationships for said battery and rate of charging to determine a value for the Internal (e.g., DC or AC) Impedance of said battery.

This process can be effected, for example, where said comparison is done by use of a look-up table having predetermined quantitative comparisons of measured capacitor charge rates and Internal (e.g., DC or AC) Impedance for a particular battery. The process may also be performed in a manner where, after determining a value for the Internal Impedance of said battery, said value for Internal (e.g., DC or AC) Impedance of said battery is used to determine a value for expended energy from said battery. In this latter process, for example, the use of the value for Internal (e.g., DC or AC) Impedance of said battery to determine a value for expended energy may be effected by reference to a graphic representation of a relationship between Internal (e.g., DC or AC) Impedance of said battery and energy expended from said battery.

This process may be performed where the storage capacitor is used to store energy which is used to energize a pace from said pacing system to a patient, or the storage capacitor has another function within the pacing system, or where the storage capacitor has no function except for its use in assisting in the determination of a charge storage rate effected by said battery.

The process may use a period immediately following an atrial pace or atrial pulse (e.g., where a pace has been inhibited) or a period immediately following a ventricular pace or ventricular pulse.

DETAILED DESCRIPTION OF THE INVENTION

The term "lithium-type" as used herein refers to the lithium iodine battery as well as other lithium systems such as those disclosed in the aforementioned article of Parsonnet et al. More broadly, the term "lithium-type" refers to a battery or cell having approximately the characteristics displayed by the lithium iodine battery. The cell has an effective open circuit voltage $E_0$ which, by way of illustration, is about 2.8 volts for the Catalyst Research battery. The effective internal impedance in series with $E_0$ comprises 2 impedance components. The first impedance component, shown as $R_L$, represents the resistance to the travel of $Li^+$ ions through the LiI layer. This resistance is a direct linear function of the charge or energy drawn from the battery, such that this component is linear as a function of battery usage. As is well understood in the art, as the charge production from the battery increases (higher Milliampere Hours), the Internal impedance increases. The increased Impedance is a clear indication of the depletion of the available energy from the battery. Dependent upon the power needed for any individual use of the battery, and a particular device attached to the battery, a certain point along the curve of internal impedance versus charge depletion is reached where the battery must be replaced or that particular device will not function properly, or may not provide the advertised or announced level of performance (pacing amplitude and rate telemetry) stated in a physician's manual before ERT is declared. At that point, the device may not provide the requested operating time after ERT to allow the physician to recognize the ERT flag. This could affect the ability to schedule and surgically replace the device before a patient's safety has been jeopardized. Some devices may have a continuous drain on the power of the battery, and others, like pacemakers or other timed performance devices, have either intermittent power requirements or combine a continuous power drain for one function (e.g., to drive a microchip, microprocessor or timing circuitry) and an intermittent function (e.g., such as pacing, measuring, signaling, lighting, etc.) which has intermittent power utilization. Even with essentially continuous drain or uniform drain on a battery, there may be circuitry within the system which makes it difficult to measure total summation of energy provided by a battery or to directly measure variables in energy consumption that would directly indicate the past charge consumption and/or the remaining charge in a battery. This measurement is made even more complicated in the environment of a pacemaker, where a battery may be implanted within a patient's body, where interruption of the power source might represent a reliability hazard, and where total past power utilization can not be accurately measured as it is dependent upon so many variables, such as for example, the individual functions which may or may not be programmed into the pacemaker (e.g., atrial pacing, ventricular pacing, sensing, adaptive rate functions, etc.), the settings programmed by the doctor for the individual patient, abnormal use characteristics, variations in activity amongst patients, and the like.

Unfortunately, it is not easy to directly measure the Internal Impedance of a battery/system or to keep an accurate running total of power consumption in the system to more directly indicate ERT. It is also of uncertain risk to disconnect the electronics (as in U.S. Pat. No. 4,259,639) to take accurate readings on the level of battery depletion.

The present invention takes advantage of certain relationships within circuitry which allow for very good approximations to be made within the system of circuits and battery to estimate Impedance of the battery in situ so that the present charge depletion state of the battery can be accurately estimated. This can be accomplished with minimal or no interruption of the normal battery and device operation.

The present invention makes use of the fact that each battery and level (average quiescence or programmed pace) of power consumption provides a determinable battery resistance versus charge depletion curve. Each type of battery, with different programming and/or average demands on the battery, will produce a slightly different, but predictable curve depending upon average battery current. For example, with higher pace power usage, the battery impedance versus Q on a graph would curve up later but more sharply with respect to the total charge utilization (e.g., the number of milliampere hours) than would a more moderately programmed device. More importantly however, the length of useful life for a battery with higher rates of power consumption is less when the Internal (e.g., DC or AC) Impedance and charge depletion increases beyond a certain point, and depending upon the specific system and needs, the system may have to be replaced at a period of shorter or less total charge consumption (e.g., because of the need for more rapid and/or more frequent and/or larger units of power demanded by the system). For example, a battery in a pacemaker where the pacing function requires about 8 microamperes of current would have much greater life and more latitude with respect to available operating time after ERT declaration for replacement at a given charge depletion level, for example only, as about 1000-1500 milliampere hours than would a battery in a pacemaker requiring 80 microamperes pacing current. The period of time to extract the necessary energy from the battery to generate the pace pulse increases as the battery is depleted, and where there is a greater power/pulse demand. If the charging time exceeds the pace pulse control period (the cardiac pacing cycle), full power provision within the system will not be delivered as therapy to the patient.

The present invention actually uses this fundamental problem in the system as a basis for monitoring the past battery charge consumption and the present power and charge reserves of a battery. To effect the practice of the present invention, a system of the present invention comprises:

1) a battery,
2) a device which is powered by said battery,
3) a storage capacitor within said device,
4) a means for reading the charge stored in said storage capacitor, and
5) a means for measuring a time interval.

The invention is practiced by commencing the measurement at the end of a cardiac event (sensed or paced), measuring the increase in charge which occurs in said storage capacitor during a predetermined or measured period of time to determine a rate of capacitor charging (or directly measuring a rate of charge increase in said storage capacitor), and relating that rate of capacitor charging to an Internal (e.g., CD or AC) Impedance for the battery. After determining or controlling the background quiescent current draw (e.g., by microprocessor or supporting electronics) from the battery, that value may be directly correlated (mathematically or graphically) to the present battery charge depletion state (as later explained). Graphic or mathematical relationships may be pre-established based upon, for example, known battery characteristics, known power requirements for specific devices, specific programming imposed upon the device, and known history of the device user. In the case of a pacemaker, embedded software within the pacemaker makes estimates of post-ERT indication operating current and uses electronic look-up tables to determine the appropriate charge time or charge rate limit. Measure charge time or rates greater than the above indicated values indicate battery charge depletion equal to or grater than that required to sustain the device operation over a reasonable time period after ERT has been declared (e.g., a reasonable physician response time), or battery impedance has grown too large to meet predefined steady-state or transient demand performance criteria, for example pacing at full programmed amplitude during temporary rate adaptive pacing. Also, a doctor may easily identify what specific mathematical relationship or curve should be used for evaluating Elective Replacement Times and/or End Of Life times for specific patients and programming which he has imposed upon the system. The supporting programmer (e.g., a computer) can read out the charge time value via telemetry and charts which will directly correlate specific storage capacitor charge rates to the remaining battery charge for the purpose of indicating the trend of battery charge depletion in the form of a gas gauge, or equivalent indicator. A storage capacitor within the system may be part of the functioning mechanism of the system (e.g., fundamental to the performance of the device, such as a storage capacitor in a pacemaker in which the pacing charge builds up) or may be inserted solely for the function of measuring charge rate for the purposes of the present invention. The capacitor may also be used for some additional, non-fundamental purpose, if desired.

One of the fundamental difficulties in making measurements of the battery system, particularly in a pacemaker, is the fact that the circuitry can have many different functions which draw on the battery at various times, and which produce current and battery terminal voltage fluctuations. These variations are normal in any system, especially a pacemaker where to achieve low power, the circuitry has been designed to operate in a duty-cycled manner. But combined with multiple device functions and varying depletion rates of the battery, it is difficult to take meaningful electrical readings to assess the battery at a random time. This is one of the reasons that U.S. Pat. No. 4,259,639 disconnects the electronics of the device, so as to reduce any transient voltage/current influences.

In the present invention, a relatively transient-free period is selected in the operation of the device. When performed, the measurement is executed at the end of a cardiac event (sensed or paced). This is done in order that the measurement, which impresses as large as possible effective battery load current in order to sensitize the measurement to the battery output impedance, does not prevent the pacing supply from fully charging and delivering full pulse amplitude on the immediate subsequent cardiac pace cycle. As the device is programmed by the physician using the programmer with known functions and intervals, these periods are known to the device's embedded controls. The periods between atrial and ventricular pacing are the obvious periods to select as relatively quiescent periods. The period between the ventricular pace and the atrial pace (that is, after the ventricular pace but before the atrial pace) is usually the longest natural quiescent period in the pacing cycle as compared to the period between the atrial pace and the ventricular pace (that is, after the atrial pace but before the ventricular pace). These two relatively quiescent periods are called interface periods, the period after the ventricular pace but before the atrial pace is called the ventricular period, and the period after the atrial pace but before the ventricular pace is called the atrial period for the purposes of the present invention. In the discussion that follows, the impedance exhibited by the battery while charging the storage capacitor is referred to as $Z_{Tchg}$. It represents the average impedance of the battery while delivering charge to the storage capacitor. Since charge transfer occurs in the form of a current pulse over a short interval (e.g., 10 to 300 msec), $Z_{Tchg}$ corresponds to an AC impedance in the range of (100 to 3 Hz). While somewhat sensitive to pulse duration, $Z_{Tchg}$ is approximately equal to the small signal AC impedance evaluated at 100 Hz. By measuring the rate of charging that occurs in a storage capacitor during a particular (or collectively both portions) of an interpace period, the Internal Impedance can be accurately approximated from the known relationships for a particular battery and programming (and to a lesser extent, as previously noted, the particular pacemaker and patient). The error in the measurement due to variations in background quiescent current is further minimized by ensuring that the capacitor charging current from the battery is much larger than the absolute value of the device's quiescent operating current. Before the (charge time/charge rate) measurement is performed, the capacitor is discharged to as low a voltage level as possible, yet not so low a charge level that it cannot be fully charged within a pace period at $Z_{Tchg}=Z_{ERT}$. Another objective of discharging the battery to a low enough level is to ensure that the battery terminal voltage falls to the so-called $V_{stop}$ or brown-out voltage of the device. When the battery's terminal voltage is held at a constant value equal to the $V_{stop}$ voltage, current available from the battery is essentially constant, as shown below. In this condition, the current available for charging the measurement capacitor is essentially constant and is inversely proportional to the battery's internal impedance. The battery terminal voltage is typically bypassed or decoupled by a large capacitor to provide transient operating current demands of the pacemaker circuits. The most notable demand is usually the pacing supplies. Unless the bypass capacitor is disconnected or discharged to the $V_{stop}$ limit, charging current is provided by the decoupling capacitor and the charge time measurement will not be sensitive to the battery's internal impedance. In our implementation, the decoupling capacitor is discharged by transferring charge to the measuring capacitor before starting the actual $V_{stop}$-limit charge time measuring phase. Part of this ability to relate the Internal Impedance and the capacitor charging rate derives from the fact that during these relatively quiescent periods, the voltage across the Internal Impedance is essentially identical to the $V_{oc}$ in the circuit less the $V_{stop}$ or the so-called brown-out voltage in the device. That is:

$$V_{batt} = V_{stop}$$

Because the battery terminal voltage is equal to the brown-out protection voltage (e.g., typically between 2 and 2.8 volts, chosen for example here as 2.35 volts), one of the variables in the system (the $V_{stop}$) is fixed. While the battery's terminal is forced to the $V_{stop}$ limit, the battery outputs an essentially constant current inversely proportional to its output charging impedance, $Z_{Tchg}$, as follows:

$$I_{batt} = \frac{V_{oc} - V_{stop}}{Z_{Tchg}} \qquad \text{EQ 1}$$

The time to charge the storage capacitor, or the time to place a specific delta (change) charge on the storage capacitor, or a directly measured rate of charge buildup on the storage capacitor, provides a means for determining other desirable values for identifying the Internal Impedance in the following manner:

$$T_{chg} = \frac{\Delta Q}{I_{batt}} = \frac{C * \Delta V}{I_{batt}} \qquad \text{EQ 2}$$

Substituting $I_{batt}$ from EQ 1 into EQ 2 leads to predictive expression for $T_{chg}$ given the battery's charging impedance value $$T_{chg} = \frac{(Z_{Tchg} * C * \Delta V)}{(V_{oc} - V_{stop})} \qquad \text{EQ 3}$$

Solving for the batteries' charge time measurement impedance $Z_{Tchg}$ provides $$Z_{Tchg} = \frac{T_{chg}(V_{oc} - V_{stop})}{(C * \Delta V)} \qquad \text{EQ 4}$$

The description of a preferred implementation of the invention for a pacemaker application is presented in a progression of three steps in order that key concepts and equations can be introduced without cluttering the discussion and equations with significant but distracting factors. First, a simple capacitive charge time measurement technique for measuring the $Z_{Tchg}$ along with certain associated shortcomings is discussed. Next a series connected switch and resistance controlled by a $V_{stop}$ comparator are added to yield an improved capacitive charge time measurement. Lastly we show how the $V_{stop}$ limited charge time measurement has been successfully integrated into existing pacemaker switched capacitor pace power supply circuitry, and how the effects of the battery decoupling capacitor and background pacing current effects are accounted for in the design and equations.

A Simple Capacitive Charge Time Measurement Technique:

The capacitive charge time system illustrated in FIG. 1 is composed of the battery represented as its Thevenin equivalent open circuit voltage ($V_{oc}$) and output charging impedance ($Z_{Tchg}$), a switch (SW1), the capacitor (C) over which the charge/voltage accumulation over time is measured. An initial value of voltage ($V_I$) is established in preparation for the charge time measurement before the switch (SW1) is closed.

The exponential voltage and current relationships as a function of time for the RC circuit formed after SW1 is closed are well known elementary electronics concepts. The terminal battery voltage and current as a function of time after the switch is closed is given by EQ 5a and 5b.

$$V_{batt}(t) = V_{oc} - (V_{ox} - V_I)e^{-t/(Z_{Tchg}*C)}$$ EQ 5a $$I_{batt}(t) = ((V_{oc} - V_I)/Z_{Tchg})e^{-t/(Z_{Tchg}*C)}$$ EQ 5b The time to charge ($T_{chg}$) from $V_I$ to an arbitrary voltage $V_F$ can be determined by setting $V_{batt}(t)$ equal to $V_F$ and solving for t (EQ 6a). Furthermore this equation can be manipulated to solve for the charging impedance, $Z_{Tchg}$, from the measured charge time value $T_{chg}$ (EQ 6b)

$$T_{chg} = Z_{Tchg} * C \ln\left[\frac{(V_{oc} - V_I)}{(V_{oc} - V_f)}\right]$$ EQ 6a $$Z_{tchg} = \frac{T_{chg}}{\left(C * \ln\left[\frac{(V_{oc} - V_I)}{(V_{oc} - V_f)}\right]\right)}$$ EQ 6b While this measurement technique is simple, practical application is troublesome if the measurement is to be performed in situ with the pacemaker circuitry connected to the battery during the measurement. The initial value of the capacitor ($V_I$), which ideally is set as low as possible in order to minimize the error effect of quiescent operating currents on the capacitor charging current, must be constrained to greater than the brown-out voltage ($V_{stop}$) of the battery powered electronic circuitry. Also, in practice a large decoupling or bypass capacitor ($C_{bypass}$) is connected across the battery terminals to provide the transient charge requirements of the powered circuitry. $C_{bypass}$ interferes with the charge time measurement because as SW1 closes some of $C_{bypass}$ charge redistributes itself immediately into charging C. This reduces the charge time measurement's intended sensitivity to $Z_{Tchg}$ as the change in voltage of C is due to the $C_{bypass}$ charge and not $Z_{Tchg}$ at all. Furthermore, the presence of $C_{bypass}$ introduces an additional error term since the measurement will be sensitive to the initial voltage condition and component value tolerance of $C_{bypass}$ as well as $C_{meas}$. The initial condition on $C_{bypass}$ can fluctuate greatly during a cardiac cycle due to pacing supply charging current as well other duties cycled circuitry especially near end of life where accuracy of the measurement is most needed. Disconnecting $C_{bypass}$ during the measurement would remedy some of these problems but the required switch would have a deleterious effect on reliability and increase the possibility of inadvertent circuitry brown-out. Finally, this simple measurement technique is more sensitive to circuit operating current fluctuation than the alternate approach described next because the charging current exponentially decays throughout the measurement. As illustrated in FIG. 1, the battery current during the measurement is at its maximum possible value $I_{peak}$, only at the moment of switch closure (SW1) and then exponentially decays away after this time. The improved charge time measurement circuit discussed next maintains $I_{peak}$ current level throughout the entire charge time measurement.

Figure 2:
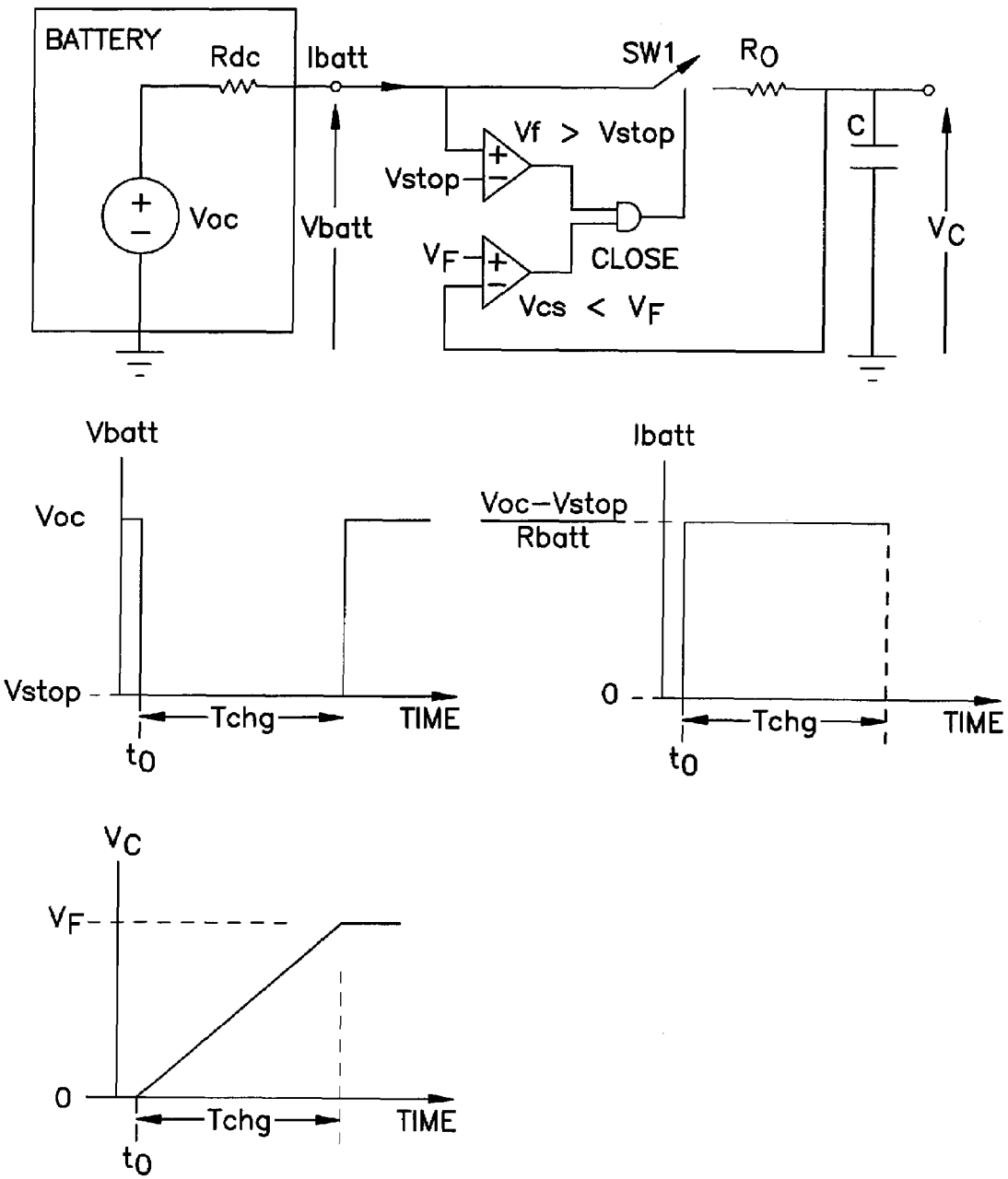
FIG. 2 shows graphic representations of Improved Capacitive Charge Time Measurement using a switched Resistor and voltage comparator.

Improved Capacitive Charge Time Measurement Using a Switched Resistor:

An improved charge time measurement system, as shown in FIG. 2, results by adding a series resistance ($R_o$) and control switch (SW1) between the battery terminal and the charge time measurement capacitor (C). Two comparators are shown in FIG. 2. The first whose output is labeled $V_{cs} < V_f$, simply indicates the charge-time measurement is complete once C has been charged to a predetermined voltage ($V_F$). This comparison is not new to the improved measurement system and was implied in the simple charge time measurement described above. The second comparator whose output is labeled $V_{batt} > V_{stop}$ we will refer to as the $V_{stop}$ comparator in the present discussion.

The $V_{stop}$ comparator and SW1 forms a feedback loop which has two purposes. First, the feedback loop prevents the battery voltage from falling below $V_{stop}$ preventing powered electronic circuitry from browning out. Secondly, for a minimum $Z_{Tchg}$, and give $R_o$, and measurement capacitor $V_F$ voltage values, the feedback loop forces the battery terminal voltage ($V_{batt}$) to constant voltage level through-out the measurement.

The measurement begins by establishing an initial voltage $V_I$ on C, which for the purposes of illustration has been arbitrarily set to zero in FIG. 2. Note that the inclusion of $R_o$ and its associated voltage drop, allows $V_I$ to be set below the brown-out voltage ($V_{stop}$) of the system, thereby avoiding one of the limitations of the simple charge time system. The charge time measurement is started by closing SW1. C begins charging toward a predetermined final voltage ($V_F$). A voltage drop develops across $Z_{Tchg}$ due to the charging current and the battery terminal voltage falls rapidly toward the $V_{stop}$ value. (Note that a battery bypass capacitor has been omitted in FIG. 2 in order to simplify the description, its effect will be discussed in more detail during the final pacemaker implementation description below.)

In FIG. 2, the $V_{stop}$ comparator samples the battery terminal voltage and opens SW1 whenever $V_{batt} < V_{stop}$ and restores the connection once $V_{batt}$ rises above $V_{stop}$ by the comparator hysteresis. This action results in an average battery terminal voltage equal to $V_{stop}$. Under this condition the average battery output current is given by EQ 8b.

$$V_{batt} = V_{stop}$$ EQ 8a $$I_{batt} = \frac{(V_{oc} - V_{batt})}{Z_{Tchg}} = \frac{(V_{oc} - V_{stop})}{Z_{Tchg}}$$ EQ 8b As illustrated in FIG. 2, the battery current during the measurement is maintained at its maximum possible value $I_{peak}$ current level throughout the entire charge time measurement. A higher sensitization current is not possible as it would result in the battery terminal voltage falling below the powered electronics brown-out voltage, $V_{stop}$.

Since the battery current is constant, the voltage across the measuring capacitor (C) charges approximately linearly with time following a ramp waveform as shown in FIG. 2. Its terminal voltage versus time during the measurement follows EQ 9.

$$V_C(t) = V_I + \frac{(I_{batt} * t)}{C} = V_I + \frac{((V_{oc} - V_{stop}) * t)}{(Z_{Tchg} * C)}$$ EQ 9

The time to charge ($T_{chg}$) from $V_I$ to an arbitrary voltage $V_F$ can be determined by setting $V_C(t)$ equal to $V_F$ and solving for t (EQ 10a). Furthermore this equation can be manipulated to solve for $Z_{Tchg}$ from the measured charge time value $T_{chg}$ (EQ 10b).

$$T_{chg} = Z_{Tchg} * C\left[\frac{(V_{oc} - V_{stop})}{(V_F - V_I)}\right]$$ EQ 10a -continued $$Z_{Tchg} = (T_{chg}/C) * \left[\frac{(V_{oc} - V_{stop})}{(V_F - V_I)}\right] \quad \text{EQ 10b}$$

Conditions for $V_{stop}$ Limit: Certain circuit conditions must exist in order that the Battery terminal voltage be driven to the $V_{stop}$ Limit and the $T_{chg}$ and $Z_{Tchg}$ expressions in EQ 10 to be valid. For example, the battery terminal voltage will not fall to the $V_{stop}$ limit if its output impedance $Z_{Tchg}$ were zero; in this case the battery terminal voltage will not deviate from $V_{oc}$. Under this condition, as described in the simple charge-time measurement system, C will charge exponentially and will yield a charge time, predicted by EQ 6b with $R_o$ taking on the role of $Z_{Tchg}$. In order to achieve "$V_{stop}$-limited" charging for a given $V_{oc}$, $V_{stop}$, $V_F$, the battery internal impedance must be greater than the minimum given in EQ 11.

$$Z_{Tchg} \geq \frac{R_o(V_{oc} - V_{stop})}{(V_{stop} - V_F)} \quad \text{EQ 11}$$

Several observations can be made from EQ 11. First, "$V_{stop}$-limited" charge times can be achieved for smaller $Z_{Tchg}$ as $R_o$ is made smaller. This will become an important consideration in our pacemaker implementation of this invention as $R_o$ is the output impedance of the pacing supply. Secondly, it is increasingly more difficult to maintain "$V_{stop}$-limited" charge times as $V_F$ approaches $V_{stop}$. In the limit, $V_F = V_{stop}$, $Z_{Tchg}$ increases to infinity in order that the charge-time remain in "$V_{stop}$-limit". Lastly, choosing a large $V_{stop}$ value has the positive effect of allowing smaller $Z_{Tchg}$ "$V_{stop}$-limited" charge times but this benefit should be balanced with the associated degradation in charge time measurement noise due to fluctuations in the powered circuitry current.

Figure 3A:
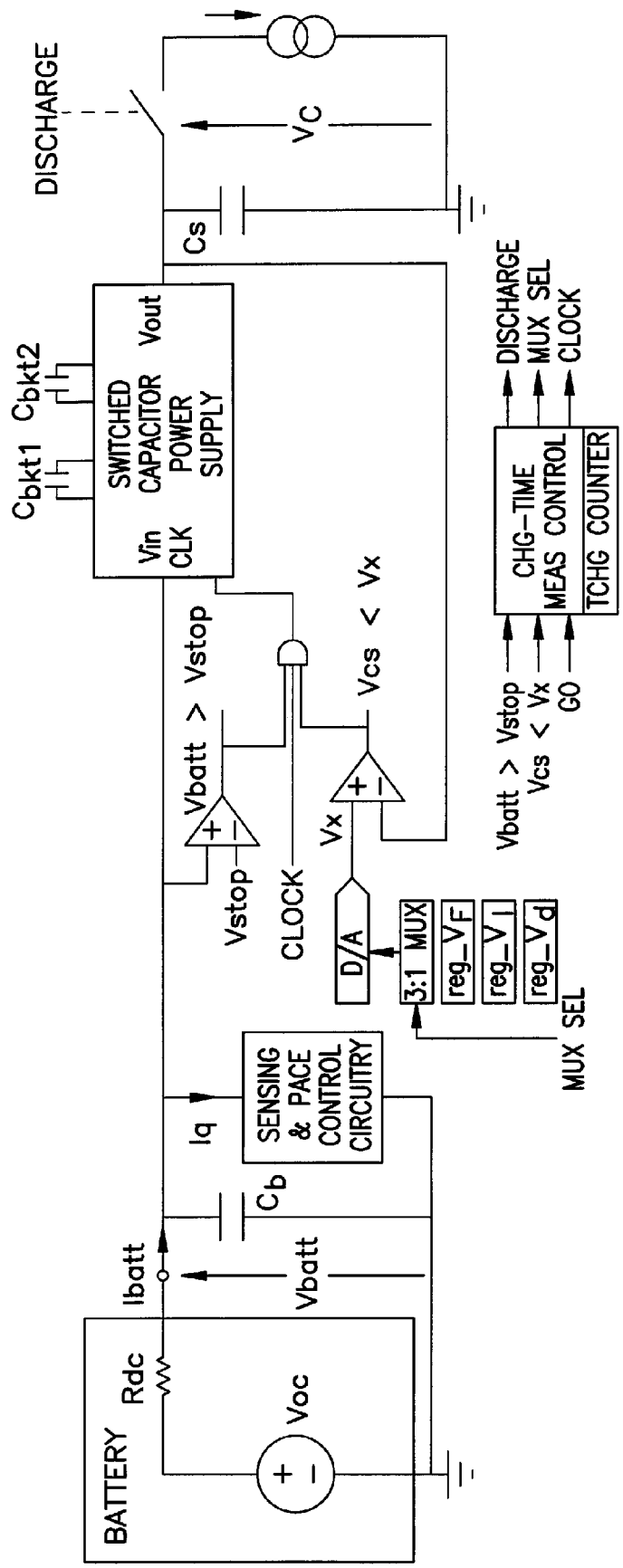

Pacemaker Capacitive Charge Time Measurement Using Pacing Supply:

The charge time measurement assessment of battery output impedance and charge depletion has been applied to a Li-Iodine battery powered pacemaker. In this preferred implementation, only a minimal amount of additional control circuitry is required beyond that already present in the pacemaker. All of the functional circuit elements of FIG. 2 already existed in modern pacemakers and can be exploited for the battery measurement system. FIGS. 3A, 3B and 3C show an example implementation using existing circuitry and components of a modern pacemaker as described next.

FIGS. 3A, 3B and 3C are an example of Pacemaker Battery Charge-time measurement Implementation. The key substitutions made in FIGS. 3A, 3B and 3C relative to FIG. 2 are:

1) Resistor $R_o$ has been replaced by the Switched Capacitor Power Supply block which exhibits an output resistance of $R_o$ when its clock is activated.

2) Switch SW1 has been replaced by the clock on-off AND gate in the middle of FIG. 3A.

3) C has been replaced by $C_s$, the pacemaker pacing supply storage capacitor from which pulsed energy is delivered to the heart.

Additional elements in FIGS. 3A, 3B and 3C relative to FIG. 2 are:

4) The battery bypass or decoupling or bypass capacitor ($C_b$).

5) A D/A converter block which is used to set the physician-programmed pace pulse amplitude output voltage level.

6) The Pacemaker Sensing & Pacing control Circuitry and an indication of its associated quiescent operating current ($I_q$).

7) The Charge-Time Measurement counter, and control logic which provides the fine control for the charge time measurement. Note that this last element represents the only additional logic required to implement the charge time measurement system in the pacemaker.

Switched Capacitor Power Supply, Output Impedance ($R_o$), and Multiplier ($K_X$-Effects on Charge Time Measurement.

Switched Capacitor power supply designs are commonly practiced and used in a variety of integrated circuit applications. In pacemakers switched capacitor power supplies are used for voltage multiplication in order to boost the Li-Iodine battery terminal voltage (~2.8V) to pacing voltage levels. These work by alternately removing charge from the battery through bucket capacitors ($C_{bkt1}$, $C_{bkt2}$) during a filling phase, and then transferring this charge to a storage capacitor ($C_s$) during the dump phase. The fill and dump phases are timed using a digital clock signal. When the digital clock is at rest no charge is transferred and an open circuit between the battery and $C_s$ exists. Therefore the switch SW1 of FIG. 2 has been functionally replaced by a "gated" clock in the pacemaker application. A number of different open circuit voltage multiplication factors are possible depending upon whether the bucket capacitors are connected in series or parallel during fill and dump phase and whether the battery is connected to the bucket capacitors during the dump phase. In the illustrated pacemaker application, the pacing supply can be programmed to voltage multiplier setting ($K_X$) of 0.5×, 1.0×, 1.5×, 2.0×, and 3.0× the terminal battery voltage. While $V_{cs}$ is less than the D/A converter $V_X$ setting, the power supply clock control is enabled and it performs fill-dump cycles continuously to charge $C_s$. While the clock is enabled, the power supply exhibits an output resistance, $R_o$, given by EQ 12, where f is the frequency of the clock and C is the equivalent capacitance formed by the series or parallel connection of the bucket capacitors ($C_{bkt1}$, $C_{bkt2}$) during the dump phase; series or parallel connection depends on the voltage multiplier setting ($K_X$).

$$R_o = \frac{1}{f * C} \quad \text{EQ 12}$$

Conditions for $V_{stop}$ Limit: To achieve "$V_{stop}$-limited" charging for a given $V_{oc}$, $V_{stop}$, $V_F$, switched-capacitor $R_o$ and multiplier setting $K_X$, the battery internal resistance must be greater than the minimum given in EQ 13.

$$Z_{Tchg} \geq \frac{R_o(V_{oc} - V_{stop})}{K_X * (K_X * V_{stop}) - V_F} \quad \text{EQ 13}$$

Several observations can be made from EQ 12 for the pacemaker application. "$V_{stop}$-limited" charge times can be achieved for smaller $Z_{Tchg}$ as $R_o$ is minimized, and $K_X$ is maximized. In order to minimize $Z_{Tchg}$ in EQ 12, both $R_o$, $K_X$ must be considered at the same time since the capacitance (C) in EQ 12 depends on the bucket capacitor circuit connections during fill-dump cycles, and therefore $K_X$. For pacemaker application, $K_X$ is determined by the amount of voltage multiplication necessary to achieve the maximum pace pulse voltage amplitude specification. A maximum pace pulse amplitude specification of about 7.0V is common in the pacemaker industry and can be achieved with a Li-Iodine battery using a voltage multiplication factor of $K_X=3$, requiring two $C_{bkt}$. Since $K_X>3.0\times$ requires additional $C_{bkt}$ capacitors in a very space sensitive application it is probably more desirable to decrease $R_o$ by increasing clock frequency f, or increasing $C_{bkt}$ value.

Secondly, the value of the minimum "$V_{stop}$-limited" $Z_{Tchg}$ rises as $V_F$ approaches $K_x*V_{stop}$. In the pacemaker application achieving "$V_{stop}$-limited" charging is desirable because the charge-time result which are "$V_{stop}$-limited" will depend on the difference $(V_F-V_I)$ and not on the absolute value of the pace amplitude setting. "$V_{stop}$-limited" charge time measurement avoids amplitude dependent mapping of charge-time to the batteries' charge-time impedance, $Z_{Tchg}$, since it is desirable in some circumstances to perform pacemaker charge time measurement with $V_F$ value equal to the physician programmed pace amplitude setting.

Alternatively, the charge time measurement can be performed while the battery terminal voltage is not at $V_{stop}$ for all or a portion of the measurement. In this case, $C_s$ charging time during non-$V_{stop}$ portions of the measurement will be exponential and will depend on the absolute values of $V_I$ and $V_F$ as predicted in EQ 6a. Under non-$V_{stop}$ limited conditions mapping of the charge time measurement to battery impedance is dependent on the absolute value of capacitor voltages. Lastly, choosing a large $V_{stop}$ value has the positive effect of allowing smaller $Z_{Tchg}$ "$V_{stop}$-limited" charge times but this benefit should be balanced with the associated degradation in charge time measurement noise due to fluctuations in the powered circuitry current. Suppose, for example, a Brady Pacemaker exhibits +/−2 uA fluctuations in average quiescent operating current during the measurement and that the resulting "$V_{stop}$-limited" battery current flow (EQ 8b) is 100 uA at the maximum end-of-life battery impedance to be measured. In this case the measurement repeatability, and therefore its accuracy, will be no better than about 2% and increasing $V_{stop}$ toward $V_{oc}$ will increase the error.

Battery Bypass Capacitor (See $C_b$ in FIG. 3A) Effects:

A Brady pacemaker periodically delivers pace pulse energy to the heart. In a typical design, the pacing energy is stored on a storage capacitor ($C_s$) until the pace pulse is delivered requiring $C_s$ to be recharged after each pace pulse. For moderate battery impedances, the initial charge transferred by the pacing supply to $C_s$ during recharge comes from the battery bypass capacitor (see $C_b$ in FIG. 3A) and is quickly removed, usually within 10-20 pacing supply switched capacitor fill/dump cycles (<20 mS). Furthermore, under most pacing and battery conditions (i.e. pulse amplitude, pulse width, and pacing lead impedance, battery DC resistance, $R_{dc}$) the battery is able to charge $C_b$ back to $V_{oc}-R_{dc}*I_q$ within the cardiac pace cycle interval time. The maximum amount of charge that can be delivered to $C_s$ from $C_{bypass}$ during the recharge and the corresponding voltage change is given by EQ 13a and b.

$$Q_{cs\_max} = \frac{((V_{oc} - I_q * R_{dc} - V_{stop}) * C_b)}{K_X} \quad \text{EQ 13a}$$

$$\Delta V_{cs\_max} = \frac{((V_{oc} - I_q * R_{dc} - V_{stop}) * C_b)}{(K_X * C_s)} \quad \text{EQ 13b}$$

For the sake of illustration the parameters of EQ 13a and 13b have been assigned values in Table 1.

TABLE 1

Example Nominal Parameters.

| Parameter | Value | Comment |
|---|---|---|
| $V_{oc}$ | 2.8 V | Open Circuit Battery Voltage |
| $I_q$ | 12 uA | Device Quiescent Current, not counting pacing current |
| $Z_{Tchg}$ | 7.0 kohms | Max battery charge time impedance; close to device replacement time |
| $C_b$ | 33 uF | Battery Decoupling Capacitor |
| $C_s$ | 10 uF | Pacing Supply Storage Capacitor |
| $K_X$ | 1.5x (nom) 3.0x (meas) | Switched-Capacitor Voltage multiplier setting. |

After substituting the values of Table 1 into EQ 13 several observations can be made. First, the terminal battery voltage near end of life differs from the unloaded beginning of life voltage by only $I_q*R_{dc}=42$ mV. Therefore traditional PG end-of-life systems that rely on a quiescent battery terminal voltage measurement provide a relatively insensitive measure of the battery charge depletion; only a 0.15% voltage change from beginning of life. These systems require precise analog circuit design and are susceptible to errors due to fluctuations in quiescent and pacing supply current.

Secondly, the maximum charge provided by $C_b$ to $C_s$ is 9.0 uC (EQ 13a), or 900 mV (EQ 13b) in the $K_X=1.5$ voltage multiplier setting. For a typical pace pulse amplitude, width and cardiac lead impedance (3.5V, 0.4 S, 500 Ohms) the pacing supply requires about 4 uC per pace pulse to replenish $C_s$. Therefore near end of life when the battery impedance is high, the pacing supply draws transient charge from $C_b$ to replenish $C_s$. This "non-$V_{stop}$ limited" charge transfer from $C_b$ is potentially problematic for the charge time measurement.

Under these conditions, $C_s$ charging time will be insensitive to the battery resistance, and charge depletion. Only when the battery is so depleted that the battery terminal voltage has fallen to the $V_{stop}$ level will $C_s$ charge time become sensitive to the battery impedance and depletion condition. Unfortunately, generally the point of time at which the charge time measurement becomes sensitive to the battery condition is too late to provide adequate recognition time for the physician to schedule device replacement in the pacemaker charge-time measurement sequence described next, $C_b$ effects are eliminated sensitizing $C_s$ charge time to the battery condition without requiring $C_b$ to be disconnected from the battery which would adversely affect device reliability.

Equations 10a and 10b relating charge-time to battery impedance $Z_{Tchg}$ and conversely allowing $Z_{Tchg}$ to be calculated from the charge-time measurement can be extended to the pacemaker implantation and are given in EQ 14a and 14b.

$$T_{chg} = \frac{(C_s * K_X * (V_F - V_I))}{\left(\left(\frac{(V_{oc} - V_{stop})}{Z_{Tchg}}\right) - I_q\right)} \quad \text{EQ 14a}$$

$$Z_{Tchg} = \frac{T_{chg} * (V_{oc} - V_{stop})}{(C_s * K_X(V_F - V_I) + (I_q * T_{chg}))} \quad \text{EQ 14b}$$

Measurement Set-Up Parameter Selection and Control:

Before the charge-time measurement is executed three measurement reference voltage parameters need to be selected and loaded into the D/A register file of FIG. 3.

| | |
|---|---|
| reg_$V_F$: | This register holds the physician programmed Pacing Voltage Amplitude Setting and marks the final voltage end point of the charge time measurement |
| reg_$V_I$: | This register holds the initial voltage level at which the charge time measurement is to begin. $V_I$ is selected as small as possible so that $\Delta V = V_F - V_I$ is maximized with the constraint that charging to $V_F$ be complete by the next time a cardiac pace pulse is required. A practical maximum time limit for the entire charge time measurement may be established at the pace period corresponding to the pacemaker's maximum programmable pacing lower-rate-limit (LRL). |
| reg_$V_d$: | This register holds a voltage reference for the voltage to which $C_s$ capacitor is to be discharged to immediately after the pace pulse marking the start of the charge time measurement. $V_d$ is set to approximately $\Delta V_{cs\_max}$ (EQ 13b) lower than $V_I$. For battery impedance meeting the conditions of EQ 12, $C_b$ will discharge and its voltage will fall to $V_{stop\ while\ the\ pacing}$ supply charges $C_s$ from $V_d$ to $V_I$. Once discharged to and held against the $V_{stop}$ limit, $C_b$ is electrically inert and on average neither receives nor provides charge during the charge-time measurement. |

Measurement Control & Sequence

In this pacemaker application example of the invention, the measurement is controlled by a small amount of dedicated hardwired digital control logic (see Chg-Time Meas Control block, FIG. 3A. Once the Sensing & Pace Control block has selected appropriate parameter values for the two reference voltages $V_I$ and $V_d$ relative to the physician programmed setting $V_F$, it selects the pacing chamber for the measurement if it is a dual chamber device.

Because the V-A pace pulse delay will generally be longer and than A-V interval, performing measurement in the atrial chamber of the dual chamber device will afford the most time for battery terminal voltage to recover from alternate chamber pacing supply charging current transients. Since "$V_{stop}$-limited" charge time measurements are not sensitive to the initial condition of $C_b$, knowing the initial condition of $C_b$ is a practical consideration only in selecting $V_d$ appropriately. Overestimating $C_b$'s initial voltage condition may lead to too aggressive of a discharge voltage extracting a wall time penalty in charging from $V_d$ to $V_I$. However, underestimating $C_b$'s initial voltage and not setting $V_d$ aggressively enough can lead to charge time measurement error if the battery terminal voltage has not fallen to $V_{stop}$ at the start of the charge-time phase of the measurement. For this reason overestimating $C_b$'s initial voltage and setting $C_s$'s discharge level accordingly avoids this potential accuracy problem.

After having been enabled via the "Go" command from the Sensing & Pace Control the Chg-Time Control block coordinates the fine control over the measurement as follows:

1) The controller selects $V_X = V_F$ for the $V_{cs} < V_X$ comparison and turns off the pacing supply clock. The controller waits and synchronizes the start of the measurement sequence to the completion of the next arriving cardiac pace pulse. Note an alternate dummy pace command is provided by the sensing & pace control block if an intrinsic cardiac depolarization is detected and a cardiac pace pulse is not required for the present cardiac cycle.

2) Once the pace or dummy pace is received and the pace pulse is completed the controller closes the discharge switch while monitoring the $V_{cs} < V_X$ comparator output. Once $C_s$ is discharged to $V_d$ voltage level (see $V_{cs}$ voltage waveform FIG. 3B, time $t_d$) the controller opens the discharge switch.

3) The controller then selects $V_X = V_I$ for the $V_{cs} < V_X$ comparison and turns on the pacing supply clock. The pacing supply charges $C_s$ to $V_I$ level (see $V_{cs}$ voltage waveform FIG. 3B, time $t_{vi}$) and stops the pacing supply clock. $C_b$ is discharged and the battery terminal voltage is driven to the $V_{stop}$ limit while $C_s$ is charged (assuming the conditions of EQ 13b are satisfied).

4) The controller then selects $V_X = V_F$ for the $V_{cs} < V_X$ comparison, and enables the $T_{chg}$ counter turns on the pacing supply clock. The charge time measurement count is accumulated within the $T_{chg}$ counter while $C_s$ is charged from $V_I$ to $V_F$. Once $V_{cs}$ is charged to the $V_F$ the measurement is complete and the $T_{chg}$ counter is frozen. The measurement is retrieved by the Pace control circuitry and compared to predefined operating current dependent charge-time limits to manage the elective replacement time declaration as described next.

ERT Declaration Management Using Charge-Time Measurement

To maximize longevity while providing a minimum safe operating time after ERT declaration, operating current dependent and performance based ERT battery charge depletion targets and associated charge-time limits are established as part of the pacemaker design.

First, the device operating current range is established through analysis of quiescent circuit current drain and min and max pacing power requirements. Once determined, the operating current range is subdivided in discrete current range "bins." The bins are defined so that all PG's in the range will operate for the minimum specified time after ERT indication is set but not so long that longevity (the operating time from implant to ERT) is significantly compromised. For example the number of bins and the bin ranges can be defined to guarantee a minimum post-ERT operate time of 3 months but not greater than 4.5 months. Increasing the number of bins will reduce the difference between in bin minimum and maximum operating current, and therefore the variation in post ERT operating times. Therefore the selection of the number of bins requires a trade-off between complexity versus longevity (pre-ERT) time.

Next battery charge depletion ERT targets are established for each bin based on post-ERT operating charge requirements and other pre- and post ERT performance criteria. Performance criteria determine the maximum tolerable battery resistance at ERT. Final battery resistance ERT target for each of the operating current bins are selected to satisfy both the charge-based post ERT operating time criteria and max tolerable battery resistance performance criteria using the battery manufacturer's charge depletion versus battery resistance mathematical models. Since Li—I battery resistance as a function of charge depletion is a function of operating current, this in general involves establishing a mathematical model for an operating current representative of each bin. Once the charge depletion and corresponding battery charge-time impedance ($Z_{Tchg}$) ERT targets have been determined, charge time measurement set-up parameters and corresponding ERT charge time limits can be established that the pacemaker can easily manage. Table 2 below shows an example of a dual chamber pacemaker operating current binning, ERT battery charge-time impedance targets, and corresponding charge-time measurement set-ups and ERT declaration limits.

TABLE 2

Example of Operating Current Binning, Charge-time measurement set-up & ERT Limits

| Bin # | Lert (uA) | $V_d$* (Volts) | $V_I$* (Volts) | ERT Charge Time Limit (ms) | Battery Charge Depletion Q (mA-Hr) | Battery Charge-Time Impedance $Z_{Tchg}$ (ohms) |
|---|---|---|---|---|---|---|
| 1 | <23 | 1.0 | 0.6 | 273 | 1120 | 6278 |
| 2 | 24-36 | 1.2 | 0.8 | 294 | 1068 | 3800 |
| 3 | 37-57 | 1.5 | 1.1 | 158 | 920 | 2050 |
| 4 | >58 | 1.5 | 1.1 | 75 | 733 | 1000 |

*Relative to $V_F$

The pacemaker manages ERT flag declaration using the information in the first four columns of Table 2. The pacemaker performs a charge-time measurement approximately once a day. Before executing the charge-time measurement, the pacemaker estimates post-ERT operating current using a combination of look-up table and equation based calculation techniques based on the present pacing mode, pacing pulse settings and lead impedance. Using the current estimate, the pacemaker indexes the appropriate bin number in Table 2, selects the set-up parameters and executes the charge time measurement. The charge-time measurement result is compared to the ERT limit. ERT is declared if the last n measurements have all been larger than the limit. The ERT charge-time measurement is stored in memory where it may be retrieved for battery charge trending as described next.

Battery Charge Remaining Trending:

The charge-time measurement value and set-up parameters may be used by the pacemaker programmer to assess battery condition, estimate and display charge remaining and operate time to ERT declaration. The battery impedance $Z_{Tchg}$ may be calculated directly from EQ 14b or by table look-up based on EQ 14b. Once $Z_{Tchg}$ is known a battery charge depletion estimate can be made using standard equation or table look-up based technique using the battery manufacturer's battery impedance versus charge depletion data and formula. A graphic representation of the relationship between battery impedance ($Z_{Tchg}$) and energy expended, energy remaining, time to ERT can be made to assist the physician in estimating approximate remaining pacemaker life.

What is claimed:

1. A system, including:
   a battery power terminal for a battery;
   sensing and pacing control circuitry electrically connected to the battery power terminal;
   a pacing supply storage (PSS) capacitor electrically connected to the battery power terminal and to a discharge switch;
   comparison circuitry, including:
      a first comparator electrically connected to the battery power terminal and adapted for comparing a battery terminal voltage (Vbatt) to a brownout voltage (Vstop), the first comparator having a first comparator output;
      a second comparator electrically connected to the PSS capacitor and adapted for comparing a pacing supply storage voltage (Vcs) to at least one reference voltage (Vx), the second comparator having a second comparator output, wherein the first comparator output and the second comparator output are adapted to control current flow from the battery power terminal to the PSS capacitor; and
   charge time measurement (CTM) control circuitry electrically connected to the sensing and pacing control circuitry, the comparator circuitry and the discharge switch, the charge time measurement control circuitry being adapted to:
      access a predetermined set of charge time measurement set-up parameters and a predetermined elective replacement time (ERT) charge time limit determined from a battery resistance ERT target that corresponds to a charge depletion target;
      determine a rate of charge storage in the PSS capacitor using the predetermined set of charge time measurement set-up parameters;
      compare the determined rate of charge storage in the PSS capacitor to the predetermined ERT charge time limit for the predetermined set of charge time measurement set-up parameters; and
      declare an ERT based on a number of comparisons between the determined rate of charge storage in the charge storage capacitor and the ERT charge time limit.

2. The system of claim 1, further comprising a switched capacitor power supply operably connected to the battery power terminal and the PSS capacitor for charging the PSS capacitor, wherein an output of the comparison circuit is electrically connected to the switched capacitor power supply to control current flow from the battery power terminal to the pacing supply storage capacitor.

3. The system of claim 2, wherein the predetermined set of charge time measurement set-up parameters include:
   a physician-programmed final voltage (VF) to end a time measurement for determining the rate of charge storage in the PSS capacitor; and
   an initial reference voltage (VI) to begin the time measurement for determining the rate of charge storage in the PSS capacitor.

4. The system of claim 3, wherein a pacing supply storage voltage (Vcs) increases approximately linearly from VI to VF during the time measurement for determining the rate of charge storage in the PSS capacitor.

5. The system of claim 3, wherein:
   the CTM control circuitry includes a multiplexer for selecting one of VF and VI to be compared to a PSS capacitor voltage level (Vsc) within the control circuitry for controlling current flow from the battery power terminal to the PSS capacitor; and
   the CTM control circuitry selects VI to be compared to Vsc to begin a time charge measurement count and VF to be compared to Vsc to end the time charge measurement count.

6. The system of claim 3, wherein the CTM control circuitry includes a time charge counter for measuring a time in which a relatively constant current charges the PSS capacitor from VI to VF.

7. The system of claim 3, wherein the sensing and pacing control circuitry includes a sensing and pacing control block adapted for selecting a voltage level (Vd) to which the PSS capacitor is discharged prior to beginning the time measurement for determining the rate of charge storage in the PSS capacitor, wherein Vd is less than VI.

8. The system of claim 7, wherein the CTM control circuitry includes a multiplexer for selecting one of the VF, VI and Vd to be compared to a PSS capacitor voltage level (Vsc) within the control circuitry for controlling current flow from the battery power terminal to the PSS capacitor.

9. The system of claim 8, wherein the CTM control circuitry selects:
VF to be compared to Vsc to synchronize the beginning of the time measurement to the completion of a cardiac depolarization;
Vd to be compared to Vsc to limit the discharge of the PSS capacitor and open a PSS capacitor discharge switch;
VI to be compared to Vsc to begin a time charge measurement count after a bypass capacitor (Cb) is discharged and a battery terminal voltage (Vbatt) is driven to a brownout voltage (Vstop) limit; and
VF to be compared to Vsc to end the time charge measurement count.

10. A system, comprising:
a pacing storage capacitor;
a battery power terminal for a battery, the terminal being electrically connected to the pacing storage capacitor to charge the pacing storage capacitor;
a discharge switch electrically connected to the pacing storage capacitor; and
control circuitry electrically connected to the discharge switch to selectively discharge the storage capacitor and electrically connected to the pacing storage capacitor to detect a voltage across the pacing storage capacitor, the control circuitry to perform a time measurement for determining a rate of charge storage in the pacing storage capacitor, wherein the control circuitry is adapted to:
discharge the pacing storage capacitor to a predetermined voltage level (Vd) prior to beginning the time measurement;
detect when the voltage across the pacing storage capacitor reaches a predetermined initial voltage level (VI) to begin the time measurement, wherein VI is larger than Vd; and
detect when the voltage across the pacing storage capacitor reaches a predetermined final voltage (VF) to end the time measurement.

11. The system of claim 10, wherein the system is incorporated in a pacemaker.

12. The system of claim 10, wherein the control circuitry is further adapted to access a predetermined elective replacement time (ERT) charge time limit, and to declare an ERT based on a number of comparisons between the rate of charge storage in the pacing storage capacitor and the ERT charge time limit.

13. The system of claim 10, further comprising circuitry to control current flow from the battery power terminal to charge the pacing storage capacitor.

14. The system of claim 13, wherein the circuitry to control current flow includes a switched capacitor power supply and comparison circuitry, the comparison circuitry includes:

a first comparator electrically connected to the battery power terminal and adapted for comparing a battery terminal voltage (Vbatt) to a brownout voltage (Vstop), the first comparator having a first comparator output; and
a second comparator electrically connected to the pacing storage capacitor and adapted for comparing a pacing supply storage voltage (Vcs) to at least one reference voltage (Vx), the second comparator having a second comparator output,
wherein the first comparator output and the second comparator output are used to control to control the switched capacitor power supply to control current flow from the battery power terminal to the pacing storage capacitor.

15. The system of claim 10, further comprising a number of registers to hold a Vd value, a VI value, and a VF value, and a multiplexer for selecting one of VF, VI and Vd to be compared to the voltage across the pacing storage capacitor.

16. The system of claim 10, wherein the rate of charge storage is determined when the voltage across the pacing storage capacitor increases linearly from VI to VF.

17. A system, including:
a battery power terminal for a battery;
a pacing supply storage (PSS) capacitor electrically connected to the battery power terminal; and
control circuitry adapted to:
deliver pacing pulses using charged stored on the PSS capacitor;
measure a rate of charge of the PSS capacitor from a first predetermined voltage to a second predetermined voltage at times synchronized to occur between delivered pacing pulses; and
compare the measured rate of charge of the PSS capacitor to a predetermined elective replacement time (ERT) charge time limit determined from a battery resistance ERT target; and
declare an elective replacement time (ERT) for the battery based on the comparison between the measured rate of charge of the PSS capacitor and the predetermined ERT charge time limit.

18. The system of claim 17, wherein:
the first predetermined voltage is an initial reference voltage (VI) to begin the time measurement for determining the rate of charge storage in the PSS capacitor;
the second predetermined voltage is a physician-programmed final voltage (VF) to end a time measurement for determining the rate of charge storage in the PSS capacitor; and
the control circuitry includes a time charge counter for measuring a time in which a relatively constant current charges the PSS capacitor from VI to VF.

19. The system of claim 18, wherein the control circuitry is adapted to discharge the PSS capacitor after a delivered pacing pulse to a discharge voltage (Vd) that is less than VI, and then charge the PSS capacitor to VI, and then charge the PSS capacitor to VF.

20. The system of claim 17, wherein the control circuitry is adapted to measure a rate of voltage change as a function of time to measure the rate of charge of the PSS capacitor.

21. The system of claim 17, wherein:
the system includes an implanted device and a programmer, and the implanted device includes the PSS capacitor and the control circuitry;
the implanted device and the programmer are adapted to communicate to each other; and the programmer is adapted to receive the measured rate of charge of the PSS capacitor from the implanted device, estimate an ERT value for the battery, and display the ERT value.

22. The system of claim 21, wherein the ERT value includes a value indicative of a charge remaining for the battery.

23. The system of claim 21, wherein the ERT value includes a value indicative of an operation time remaining for the battery.

24. The system of claim 1, wherein the system includes a pacemaker, and the pacemaker includes the sensing and pacing control circuitry, the PSS capacitor, the first comparator, the second comparator, and the CTM control circuitry.

25. The system of claim 17, wherein the system includes a pacemaker, and the pacemaker includes the PSS capacitor and the control circuitry.

* * * * *

UNITED STATES PATENT AND TRADEMARK OFFICE
CERTIFICATE OF CORRECTION

PATENT NO.        : 7,580,749 B2                                         Page 1 of 1
APPLICATION NO.   : 11/779779
DATED             : August 25, 2009
INVENTOR(S)       : Michael J. Lyden It is certified that error appears in the above-identified patent and that said Letters Patent is hereby corrected as shown below:

In column 22, line 12, in Claim 14, delete "to control to control" and insert -- to control --, therefor.

Signed and Sealed this

Fifth Day of January, 2010

David J. Kappos
*Director of the United States Patent and Trademark Office*